United States Patent [19]

Tsukada

[11] 4,430,151
[45] Feb. 7, 1984

[54] METHOD OF MONITORING STATUS OF A SILICON LAYER BY DETECTING, EMISSION SPECTRA VARIABLE DURING ETCHING

[75] Inventor: Tsutomu Tsukada, Tokyo, Japan

[73] Assignee: Anelva Corporation, Tokyo, Japan

[21] Appl. No.: 502,461

[22] Filed: Jun. 9, 1983

[30] Foreign Application Priority Data

Jun. 11, 1982 [JP] Japan ................................ 57-100415

[51] Int. Cl.³ .................... H01L 21/306; C03C 15/00; C03C 25/06; B44C 1/22
[52] U.S. Cl. ................................. 156/626; 156/345; 156/643; 156/646; 156/662; 204/192 E; 356/425; 356/437
[58] Field of Search ............... 156/626, 627, 643, 646, 156/657, 659.1, 662, 345; 252/79.1; 427/38, 39; 118/620; 204/164, 192 E, 298; 356/412, 414, 416, 425, 437

[56] References Cited

U.S. PATENT DOCUMENTS 4,289,188 9/1981 Mizutani et al. ..................... 156/626
4,367,044 1/1983 Booth et al. ......................... 356/357

Primary Examiner—William A. Powell
Attorney, Agent, or Firm—Laff, Whitesel, Conte & Saret

[57] ABSTRACT

In a monitoring method of monitoring status of a silicon layer etched in a hollow space by plasma, a chlorine including gas is introduced into a hollow space to cause CCl-radical to occur in the hollow space. A first spectrum region is selected to detect first emission spectra of the CCl-radical which are variable in intensity only during the etching and which may include a wavelength of 307 nm. Preferably, a second spectrum region is selected to second emission spectra invariable even during the etching and to indicate the beginning and the end of the etching by monitoring a relationship between the first and the second emission spectra. The second spectrum region may include a wavelength of 396 nm. Alternatively, emission spectra of OH-radical which results from water remaining in the hollow space may be monitored as the first emission spectra.

13 Claims, 2 Drawing Figures

METHOD OF MONITORING STATUS OF A SILICON LAYER BY DETECTING, EMISSION SPECTRA VARIABLE DURING ETCHING

BACKGROUND OF THE INVENTION

This invention relates to a monitoring method for use in a dry etching method of etching a silicon layer, so as to monitor status of the silicon layer.

A dry etching method of the type described is for use in etching a layer by the use of plasma resulting from a glow discharge in a gas filled in a hollow space. More specifically, such etching operation is advanced by virtue of various kinds of species activated in the plasma.

The dry etching method becomes indispensable for manufacturing a wide variety of semiconductor circuits, with development of a semiconductor integration technique. On manufacturing the semiconductor circuits, a silicon layer of, for example, polycrystalline silicon should often be etched as the layer by a dry etching method. It is very important to etch such a silicon layer on large scale integration or very large scale integration of MOS transistors, each having a gate electrode of polycrystalline silicon.

A conventional dry etching method uses a fluorine including gas in order to etch the silicon layer. With this method, isotropic etching is progressive and results in degradation of a precision of the etching. In addition, an etch rate is prone to be variable due to fluctuation of an electric field produced in the hollow space and the like.

In order to make anisotropic etching progress, another dry etching method makes use of a chlorine including gas. Such anistropic etching enables an improvement of the precision of etching. However, the etching rate is variable with this method also. It is therefore necessary to monitor the status of the silicon layer and to precisely detect the end of the etching. Otherwise, undercuts and the like inevitably takes place in the silicon layer. This is because a concentration of the activated species is rapidly increased after completion of the etching.

In a conventional monitoring method, a spectrum analysis is used to detect the end of the etching. The conventional monitoring method monitors emission spectra resulting from Si-radical and SiCl-radical. Such emission spectra are however susceptible to disturbance by any other emission spectra resulting from the remaining species.

For example, the Si-radical has spectrum components at 288.1 nm and 252.8 nm while the SiCl-radical has a spectrum component at 245 nm. On the other hand, carbon tetrachloride which is used as the chlorine including gas has emission spectra superposed on all of the above-mentioned spectrum components.

SUMMARY OF THE INVENTION

It is an object of this invention to provide a monitoring method which is capable of readily monitoring status of a silicon layer when the silicon layer is etched by a dry etching method.

It is another object of this invention to provide a monitoring method of the type described, which is capable of detecting the end of the etching.

A method to which this invention is applicable is for use in etching a layer of silicon by plasma in a chlorine including gas filled in a hollow space, to distinguish between a first and a second duration which the layer is being etched and not, respectively. The plasma producing CCl- and OH-radicals which result from the chlorine including gas and from water remaining as a remnant in the hollow space, respectively. According to this invention, the method comprises the steps of selecting emission spectra which result from a preselected one of the CCl- and the OH-radicals and which are variable in intensity at a transition time instant between the first and the second durations and monitoring the intensity of the emission spectra to detect the transition time instant and to, thereby, distinguish between the first and the second durations.

DESCRIPTION OF THE PREFERRED EMBODIMENTS

Figure 1:
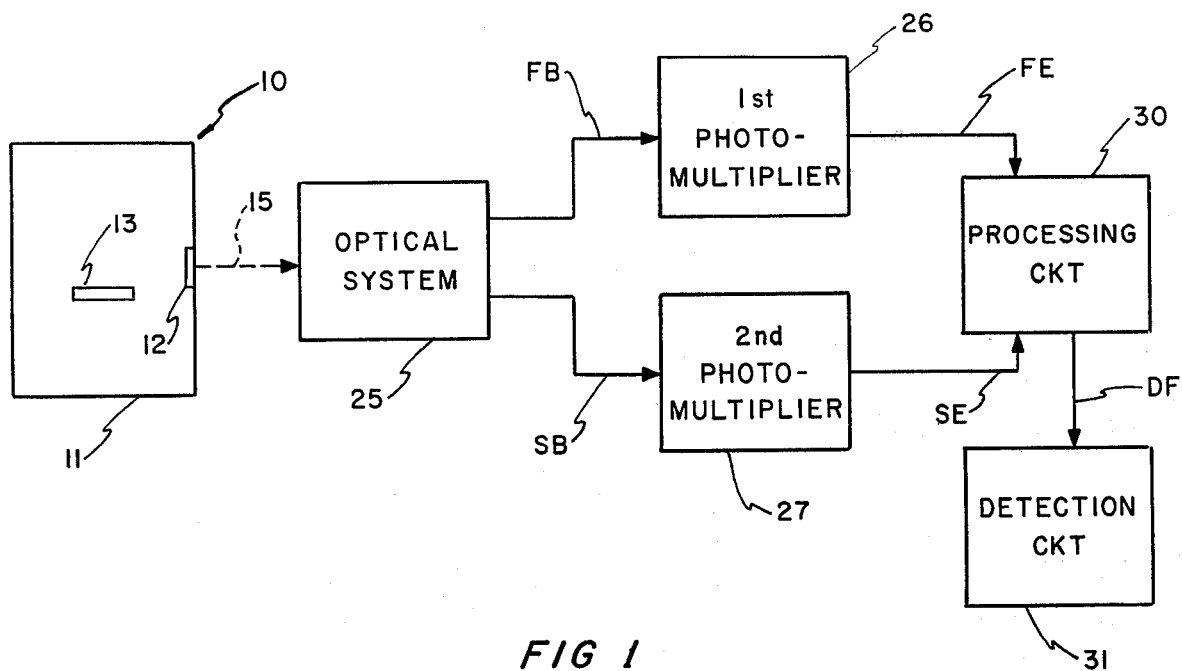
FIG. 1 shows a block diagram of a monitoring device to which this invention is applicable, together with a dry etching device.

Referring to FIG. 1, a monitoring device to which this invention is applicable is for use in combination with a dry etching device 10. The dry etching device 10 comprises a chamber 11 defining a hollow space and a single window 12 attached to the chamber 11. A layer 13 of silicon may be of polycrystalline silicon and is placed in the hollow space to be etched by the dry etching device 10. Such a polycrystalline layer is often formed to manufacture a semiconductor circuit comprising a great deal of metal-oxide-semiconductor (MOS) transistors each of which has a gate electrode of polycrystalline silicon. The hollow space is filled to a pressure of 0.1 Torr with a chlorine including gas. The chlorine including gas may be a mixed gas of carbon tetrachloride (CCl$_4$), helium, and oxygen.

A glow discharge is caused to occur in the hollow space in the known manner. As a result, plasma takes place in the hollow space and activates various kinds of species including carbon monochloride radical (CCl-radical) and hydroxyl radical (OH-radical). The CCl- and the OH-radicals result from dissolution of the mixed gas and water due to the plasma, respectively. Water inevitably remains as a remnant in the hollow space.

A light beam 15 is taken out through the window 12. A spectrum analysis of the light beam 15 is carried out in the known manner. As a result, it has been formed by the inventor that emission spectra resulting from CCl-radical become weak in intensity in a first spectrum region including a wavelength of 307 nm during the etching of the silicon layer 13. In other words, the emission spectra in the first spectrum region are therefore be variable only during the etching. The first spectrum region has a bandwidth of 20 nm between 297 nm and 317 nm. The reason why the emission spectra of the CCl-radical becomes weak is that the CCl-radical reacts with the silicon in compliance with the following:

$$4CCl + Si \rightarrow SiCl_4 + 4C,$$

and that a concentration of the CCl-radical becomes thin during the etching of the silicon.

According to the inventor's experimental studies, invariable emission spectra has been found at a second spectrum region including a wavelength of 396 nm even when the silicon layer 13 is being etched. Such a second spectrum region has a bandwidth of 20 nm, as is the case with the first spectrum region. The invariable emission spectra result from any other species than the CCl-radical.

Thus, it is also possible to monitor the status of the silicon layer 13 by processing the variable emission spectra with reference to the invariable emission spectra. Such processing may be for calculating a difference between the intensities of the variable and the invariable emission spectra, a square of the difference, and a ratio between the intensities of the variable and the invariable emission spectra. The difference will be calculated in the illustrated monitoring device in a manner to be described.

Figure 2:
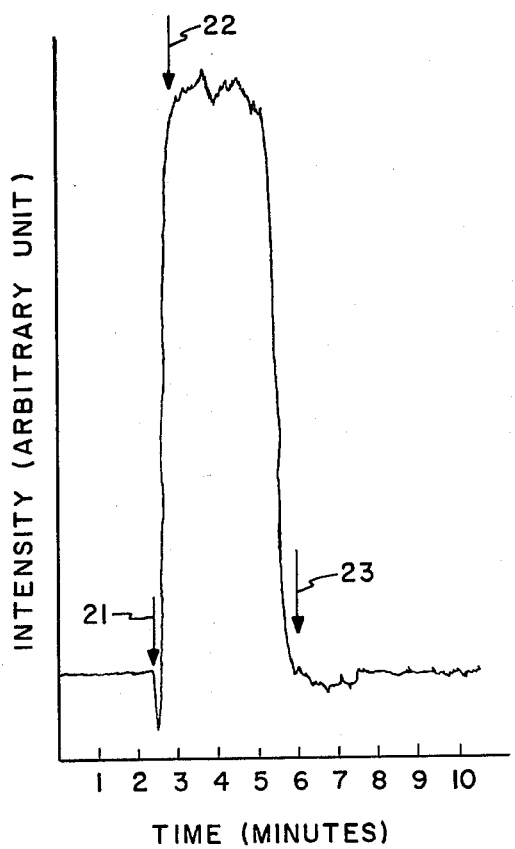
FIG. 2 shows a graphical representation for describing operation of the monitoring device illustrated in FIG. 1.

Referring to FIG. 2, the difference between the variable and the invariable emission spectra is kept at a substantially invariable level or a low level prior to the etching of the silicon layer 13. When a glow discharge begins at the first time instant 21, the difference sharply rises up to a high level as shown at the second time instant 22. This is because the intensity of the variable emission spectra is reduced relative to that of the invariable emission spectra when the etching of the silicon layer 13 begins at the second time instant 22. The difference is kept at the high level during the etching and is reduced to a low level at the end of the etching of the silicon layer 13, as shown at a third time instant 23.

Inasmuch as the difference remains at the high level only during the etching of the silicon layer 13, it is possible to detect the beginning and the end of the etching which are specified by the second and the third time instants 22 and 23.

Referring back to FIG. 1, the monitoring device is for monitoring the status of the silicon layer 13 to distinguish between first and second durations during which the silicon layer 13 is being etched and not, respectively. In other words, the monitoring device is for use in detecting the beginning and the end of the etching. For this purpose, the above-mentioned facts or findings will be utilized with the monitoring device in a manner to be described later.

The light beam 15 is incident to an optical system 25 to be divided into first and second split beams FB and SB comprising first and second spectrum components, respectively. The first and the second spectrum components FB and SB for providing the variable and the invariable emission spectra in the first and the second spectrum regions, respectively.

The first and the second split beams FB and SB are sent to first and second photomultipliers 26 and 27 to be converted into first and second electric signals FE and SE having first and second voltage levels proportional to the intensities of the first and the second spectrum components, respectively. Responsive to the first and the second electric signals FE and SE, a processing unit 30 calculates a level difference between the first and the second voltage levels to produce a difference signal DF representative of the level difference. As readily understood, the level difference is varied during the etching of the silicon layer, as described in conjunction with FIG. 2.

A detection circuit 31 monitors the difference signal DF to detect the second and the third time instants 22 and 23 specifying the beginning and the end of the etching, respectively. Such detection of the second and the third time instants is possible by comparing the difference signal DG with a reference signal having a reference level, as shown in the art.

It has also been found that emission spectra of the OH-radical are reduced in intensity during the etching of the silicon layer 13 within a prescribed spectrum region. The prescribed spectrum region includes a wavelength of 307 nm, like in the CCl-radical. This is because silicon tetrachloride (SiCl$_4$) reacts during the etching with water remaining in the hollow space. The reaction of SiCl$_4$ with water is given by:

$$SiCl_4 + H_2O \rightarrow SiO_2 + HCl.$$

Thus, the above-mentioned reaction results in a reduction of a partial pressure of the water and makes the emission spectra of the OH-radical weak during the first duration. In addition, SiCl$_4$ takes place as a result of reaction of the silicon with chlorine chemisorbed in the silicon layer 13.

From this fact, it is readily understood that the end of the etching can be detected by monitoring the emission spectra of the OH-radical.

Each of the CCl- and OH-radicals have emission spectra spread over a wide spectrum region. It is possible to monitor as the first and the second spectrum components any other spectrum regions than the spectrum regions including wavelengths of 307 nm and 396 nm, if the emission spectra are varied only during the etching.

While this invention has thus far been described in conjunction with a few embodiments thereof, it will readily be possible for those skilled in the art to put this invention into practice in various manners. For example, the processing circuit 30 may calculate a square of the level difference and/or a ratio of the first and the second electric signals FE and SE. Alternatively, the first spectrum component alone is directly monitored by the detection circuit 31. The chlorine including gas may be CCl$_3$F, CCl$_2$F$_2$, or the like. The silicon layer 13 may be of single crystal silicon, polycrystalline silicon including at least one of phosphorus, boron, and arsenic.

What is claimed is:

1. A method for use in etching a layer of silicon by plasma in a chlorine including gas filled in a hollow space, to distinguish between a first and a second duration which said layer is being etched and not, respectively, said plasma producing CCl- and OH-radicals whch result from said chlorine including gas and from water remaining as a remnant in said hollow space, respectively, said method coprising the steps of:

selecting emission spectra which result from a preselected one of said CCl- and said OH-radicals and which are variable in intensity at a transition time instant between said first and said second durations; and monitoring said intensity of said emission spectra to detect said transition time instant and to, thereby, distinguish between said first and said second durations.

2. A method as claimed in claim 1, wherein said preselected radical is said OH-radical, the emission spectra of said OH-radical being laid in a predetermined spectrum region.

3. A method as claimed in claim 2, wherein said predetermined spectrum region includes a wavelength of 307 nm.

4. A method as claimed in claim 1, wherein said preselected radical is said CCl-radical, the emission spectra of said CCl-radical being laid in a prescribed spectrum region.

5. A method as claimed in claim 4, wherein said prescribed spectrum region includes a wavelength of 307 nm.

6. A method as claimed in claim 1, wherein said chlorine including gas comprises carbon tetrachloride.

7. A method as claimed in claim 6, wherein said chlorine including gas further comprises at least one additional gas selected from a group consisting of inert gases, an oxygen gas, and a nitrogen gas.

8. A method as claimed in claim 7, wherein said additional gas comprises a helium gas.

9. A method as claimed in claim 8, wherein said additional gas further comprises said oxygen gas.

10. A method as claimed in claim 1, wherein said layer comprises polycrystalline silicon.

11. A method as claimed in claim 10, wherein said layer comprises at least one of phosphorus, boron, and arsenic doped in said polycrystalline silicon.

12. A method as claimed in claim 1, further comprising the step of:

further selecting additional spectra invariable in intensity at said transition time instant;

said monitoring step comprising the steps of:

detecting a relationship between the intensities of said emission spectra and said additional emission spectra; and distinguishing between said first and said second durations in consideration of said relationship.

13. A method as claimed in claim 12, wherein said additional emission spectra comprises a spectrum region including a wavelength of 396 nm.

* * * * *